(12) United States Patent
Hur (10) Patent No.: US 7,587,023 B2
(45) Date of Patent: Sep. 8, 2009

(54) METHOD AND APPARATUS FOR ACHIEVING OPTIMAL RADIATION DOSE IN CORONARY CT ANGIOGRAPHY USING STANDARD DEVIATION OF CT NUMBER

(76) Inventor: Gham Hur, 304-502 Hosoo apt., Janghang-dong, Ilsandong-ku, Goyang-si, Kyunggi-do (KR)

( * ) Notice: Subject to any disclaimer, the term of this patent is extended or adjusted under 35 U.S.C. 154(b) by 3 days.

(21) Appl. No.: 11/738,027

(22) Filed: Apr. 20, 2007

(65) Prior Publication Data

US 2007/0258559 A1 Nov. 8, 2007

(30) Foreign Application Priority Data

Apr. 20, 2006 (KR) .................. 10-2006-0035735

(51) Int. Cl.
*G01N 23/083* (2006.01)
*H05G 1/34* (2006.01)
(52) U.S. Cl. .................. 378/16; 378/8; 378/110
(58) Field of Classification Search .................. 378/4, 378/8, 16, 18, 19, 95, 98.8, 98.11, 98.12, 378/109, 110, 114–116
See application file for complete search history.

(56) References Cited

U.S. PATENT DOCUMENTS 7,106,824 B2* 9/2006 Kazama et al. ............. 378/16
7,203,270 B2* 4/2007 Okumura et al. ........... 378/16
7,215,733 B2* 5/2007 Nabatame .................. 378/16

* cited by examiner

*Primary Examiner*—Edward J Glick
*Assistant Examiner*—Thomas R Artman
(74) *Attorney, Agent, or Firm*—Oblon, Spivak, McClelland, Maier & Neustadt, P.C.

(57) ABSTRACT

A radiation dose modulation apparatus controls radiation dose in coronary CT angiography that utilizes an X-ray CT system including a multi-row detector. The apparatus is provided with a tube current modulation table storage unit which classifies standard deviation values of CT numbers calculated from a pre-contrast cardiac CT image into a number of levels, and stores a table in which the levels correspond to tube current modulation values, and a processing unit which calculates standard deviations of CT numbers from at least one pre-contrast cardiac image, identifies the tube current value corresponding to the standard deviations from the tube current modulation table, and controls a scan operation at the time of CT imaging for obtaining a post-contrast coronary image in accordance with the identified tube current value.

12 Claims, 5 Drawing Sheets

METHOD AND APPARATUS FOR ACHIEVING OPTIMAL RADIATION DOSE IN CORONARY CT ANGIOGRAPHY USING STANDARD DEVIATION OF CT NUMBER

CROSS-REFERENCE TO RELATED APPLICATIONS

This application is based upon and claims the benefit of priority from prior Korean Patent Application No. 10-2006-0035735, filed Apr. 20, 2006, the entire contents of which are incorporated herein by reference.

BACKGROUND OF THE INVENTION

1. Field of the Invention

The present invention relates to a method and an apparatus for individually modulating a tube current of an X-ray computerized tomography (CT) system in CT examination of the heart that uses multi-row detector.

2. Description of the Related Art

In general, cardiac CT for coronary artery evaluation is used to observe calcification of coronary arteries by carrying out CT scan before administration of contrast medium (hereinafter, referred to as "pre-contrast"), and then, to determine a precise scan range (Z axis) and positions (X and Y axes). The imaging to observe this calcification is called calcium scoring CT imaging. It is typical to use a prospective ECG gating (electrocardiogram: hereinafter, referred to as ECG) technique and a Half-reconstruction technique (a technique for reducing a radiation dose and enabling image construction with only information obtained during about 180-degree rotation).

After the pre-contrast imaging, CT scan is carried out after the administration of the contrast medium (hereinafter, referred to as "post-contrast. In post-contrast imaging (image observed after blood vessels are enhanced by a contrast medium), typically a retrospective or prospective ECG gating technique (a technique for obtaining images with ECG signals that are outputted from heart and selecting heart phases with comparatively small motion) is used. The two studies (pre-contrast and post-contrast) show a significant difference in radiation dose. In such coronary CT angiography, coronary arteries, which are the targets for the CT angiography, are located on a surface of a heart, and move at a high speed (60 to 70 times per minute) by repeated contraction and relaxation of the heart. The size of the coronary arteries that need to be visualized is very small, and thus a technique for imaging them is complicated and cumbersome, and strongly depends on a variety of scan methods. With recent development of multi-row detector CT, indications as well as diagnostic precision have been improved, the frequency of such angiography has increased, and consequently, harmfulness relevant to radiation defined as a carcinogen has further emerged.

Recently, in addition to a technique of a CT system including a multi-row detector, there has been improved precision for finding significant coronary stenosis by means of coronary CT angiography with development of a technique for imaging a moving heart (significant coronary stenosis used here denotes stenosis of 50% or more).

Such an advantageous effect has been a great interest of researchers or the like in research for quantification of coronary stenosis and evaluation of usefulness of coronary CT angiography for analyzing constituent components of soft plaque observed in a patent who is prone to suffer from an acute heat attack (soft plaque: a substance generated on a blood vessel wall and mainly formed of a lipid core of which collagen-rich fibrous plaque or fat is a main substance, unlike calcified hard plaque).

In general, in an X-ray CT system that includes a multi-row detector and carries out helical scan imaging, an operator sets an imaging condition suitable for a patient before imaging, and the imaging condition is sometimes varied depending on objects to be imaged or purposes for which imaging is carried out. Namely, a variety of parameters such as tube voltage, tube current, X-ray beam thickness, size of FOV (field of view), image reconstruction slice thickness, helical pitch (speed of table movement), reconstruction algorithm, patient position, beam hardening, and method of ECG gaiting are set in accordance with the imaging condition, and then, a radiation dose for the patient is displayed under the selected imaging condition, thereby making it possible for a person who reads an image to judge adaptability of the imaging condition.

In general, in the X-ray CT system including a multi-row detector, a predetermined dose has been used in accordance with a body part to be examined, or the dose is determined by a measurement obtained from the patient such as weight, height or body dimensions, or the dose can be determined by a scout view (scout image: an image similar to that obtained by general X-ray imaging that is not tomography imaging, and acquired without rotation of X-ray tubes). However, with respect to such values, a practical image noise level becomes greater or smaller than an image noise value expected under a predetermined scan condition, depending on differences with respect to each subject in the size of imaging sites or differences in morphological structure as well as tissue type. Therefore, there has been a problem that, if the practical image noise amount is greater than an allowable value, required diagnostic image quality cannot be obtained. In addition, there has been a problem that, in the case where the practical image noise level is smaller than an allowable value for diagnostic quality, the X-ray exposure dose becomes greater than is ideally necessary. Automatic tube current modulation (ATCM), that utilizes attenuation information from scout view(s) has been used for CT imaging of body that has a long scan range with variable attenuation, but it is not suited for CT of the heart that has short scan range with relatively uniform attenuation. In addition, since it dose not use information directly from reconstructed CT image that is a result of the use of various imaging conditions and methods described above, it does not accurately modulate radiation dose of post-contrast image.

Among the different types of CT studies, the reduction of radiation exposure is particularly important in coronary CT angiography. It uses relatively large radiation dose (equivalent to 300-650 chest x-ray examinations). It has been difficult to avoid X-ray exposure to the breasts, which are sensitive to radiation. Because of their anatomical position, it has been difficult to carry out precise measurement based on an element such as body weight, especially when there are individual differences in the size of the breasts and in the type of tissue (gland or fat) that is present, and there has been a need for precise modulation by the use of a standard deviation of CT number (also called Hounsfield number) directly obtained from reconstructed pre-contrast images that reflects scan parameters as well as size and tissue type of imaging part (heart and overlying breasts). The exponential relationship between body size, radiation dose and noise (standard deviation of CT number has long been established (Formula 1) and used for measurement of noise level on reconstructed image that contain homogenous fluid or tissue.

BRIEF SUMMARY OF THE INVENTION

It is an object of the present invention to provide an accurate method and an easy to use apparatus for modulating an X-ray exposure dose, thereby mostly reducing or increasing exposure to subject, while enabling an image of uniform optimal image quality.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

More particularly, the present invention relates to a method and an apparatus for modulating an X-ray tube current by utilizing a standard deviation of CT values in coronary CT angiography.

The multi-row detector CT system is capable of acquiring images of uniform quality in coronary CT angiography by X-ray tube current modulation, utilizing a standard deviation of CT numbers calculated by performing direct measurement, from CT images before administration of a contrast medium, and then, adjusting a radiation dose for optimal quality of the post-contrast image. In addition, uniformity in quality of images will help improve accuracy of diagnosis because it allows the characterization of tissue type to be more precise (through the greater precision of threshold settings of CT numbers).

In particular, the present invention relates to a method and an apparatus for controlling a radiation dose to optimize tube current and obtain image quality necessary for diagnosis. The modulation can be carried out during post contrast CT studies at body locations that meet certain requirements. First, the imaging location must contain a homogenous fluid of sufficient amount at its central area. Second, there must be a short scan range in which attenuation relevant to the Z-axis (the axis for linking upper and lower parts of the body) hardly varies. Such requirements are met, among other places, in the heart, where cardiac chambers and aortic root, especially the left atrium contains homogenous blood, and the scan range relevant to the Z-axis hardly varies. Having met these requirements, the modulation itself is carried out by creating a conversion table by imaging set of phantoms under the same condition as a practical scan conditions (parameters) including type of ECG gaiting and other variables mentioned above; and using the standard deviation of CT numbers relative to an image obtained from a pre-contrast left atrium in coronary CT angiography as a practical intervening variable for tube current modulation of a CT system after injecting contrast medium.

BRIEF DESCRIPTION OF THE SEVERAL VIEWS OF THE DRAWING

The accompanying drawings, which are incorporated in and constitute a part of the specifications, illustrate embodiments of the invention, and together with the general description given above and the detailed description of the embodiments given below, serve to explain the principles of the invention.

DETAILED DESCRIPTION OF THE INVENTION

Figure 1:
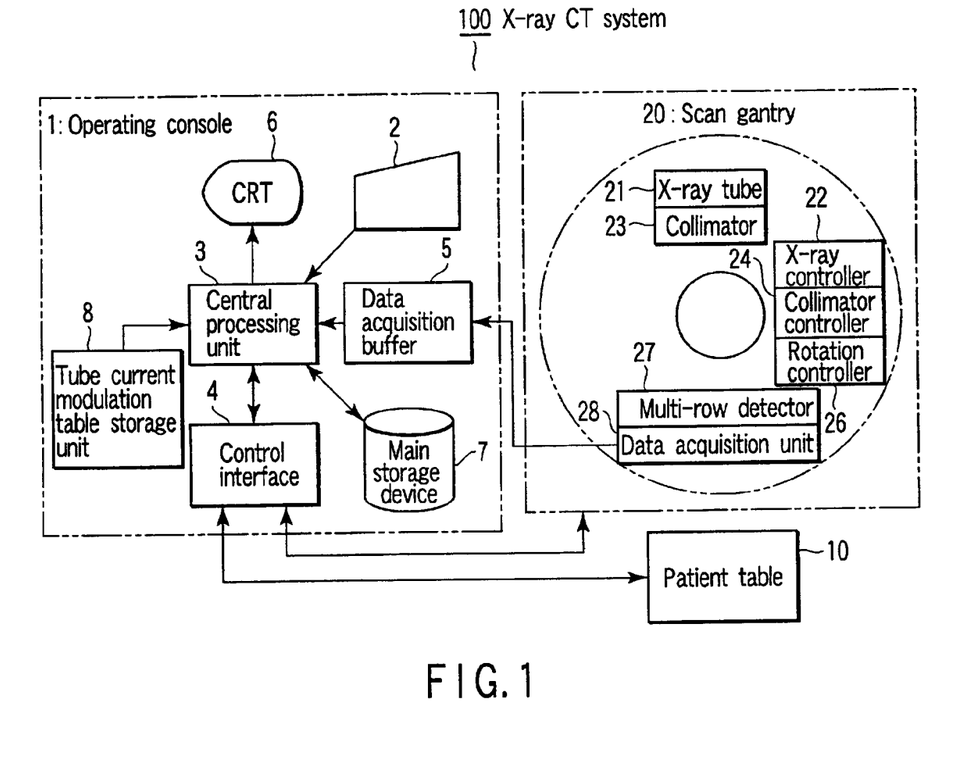
FIG. 1 is a block diagram depicting a schematic configuration of an X-ray CT system for use in coronary CT angiography according to the present invention.

FIG. 1 is a block diagram illustrating a schematic configuration of an X-ray CT system for use in coronary CT angiography according to the present invention, wherein, as illustrated in the drawings, an X-ray CT system (100) includes an operating console (1), a patient table (10), and a scan gantry (20). The operating console (1) includes: an input device (2) which inputs commands or information supplied by an operator; a central processing unit which controls X-ray exposure with an X-ray tube (23) by utilizing the commands or information inputted through the input device, calculates CT numbers and a standard deviation thereof from at least one precontrast coronary image received through a data acquisition buffer (5), samples from a tube current modulation table a tube current value that corresponds to the standard deviation of the calculated CT numbers, and executes a scan control process for controlling, by means of the sampled tube current value, a scanning operation at the time of tomography imaging for obtaining a post-contrast coronary image; a control interface which exchanges a control signal or the like with the patient table (10) and the scan gantry (20); the data acquisition buffer (5) which acquires data acquired in the scan gantry (20); a display section (6) which displays a tomographic image restored from data; a main storage device (7) which stores operation control programs for controlling a whole operation of the operating console, associated data, and X-ray tomographic images; and a tube current modulation table storage section (8) which classifies the standard deviation values of the CT numbers that can be calculated from a pre-contrast coronary image into a number of levels, and then, stores a table having preset the tube current modulation values that correspond to the respective levels.

In tube current modulation table, the standard deviation values of CT numbers may be replaced with another noise index as the value in which the level of the noise of the image is shown. Moreover, a parameter to decide the tube current may be stored as tube current information instead of the tube current value. In this case, the tube current value is determined from this tube current information.

The tube current modulation table stored in the tube current modulation table storage section (8) is illustrated in Table 1 below. For the CT scan, several tables may be stored to corresponding scan parameters such as FOV, tube current and reconstruction thickness.

In particular, Table 1 of the present embodiment illustrates a form in which the tube current modulation values have been classified into three stages with respect to the standard deviations of the respective levels. In the figure, three levels of the image noise (SD 13, 12, 11) to be obtained in post-contrast images but table with more levels can be calculated using same method so that the tube current modulation values correspond to the respective image noise levels. A coronary image having the thus obtained image noise level can be selectively obtained.

TABLE 1

Tube Current Modulation Table

| SD at 300 mA | Level of desired noise in SD and mA required* | | |
|---|---|---|---|
| | SD 13 | SD 12 | SD 11 |
| 7 | 150 | 150 | 150 |
| 8 | 150 | 150 | 170 |
| 9 | 150 | 175 | 200 |
| 10 | 180 | 210 | 240 |
| 11 | 22 | 250 | 300 |
| 12 | 250 | 300 | 350 |
| 13 | 300 | 340 | 400 |
| 14 | 335 | 380 | 435 |
| 15 | 375 | 425 | 480 |
| 16 | 420 | 475 | 500 |
| 17 | 450 | 500 | 500 |
| 18 | 500 | | |

Left column indicate standard deviation of CT numbers measured from the left atrium on the precontrast image scanned at 300 mA. Three levels of image quality (noise level) were provided in this table. The numbers in bold represent maximum tube current and may not generate image quality of desired noise level. The underlined numbers indicate minimum tube current tested and may produce better image quality than desired noise level.

On the other hand, the scan gantry (20) includes: an X-ray tube (21); an X-ray controller (22); a collimator (23); a collimator controller (24); a rotation controller (26) which rotates the X-ray tube (21) around the center of a scan; a multi-row detector (27) having an array of a number of detectors arrayed in parallel; and a data acquisition section (28) which acquires data sampled from the multi-row detector. The X-ray radiated from the X-ray tube (21) collides with the top of each detector array of the multi-row detector (27) in the form of flat X-ray beams after passing through an aperture of the collimator (23), and, if data is sampled from the multi-row detector (27), the sampled data is acquired by means of the data acquisition section (28), so that the data can be provided to the central processing unit (3) through the data acquisition buffer (5) of the operating console (1).

Figure 2:
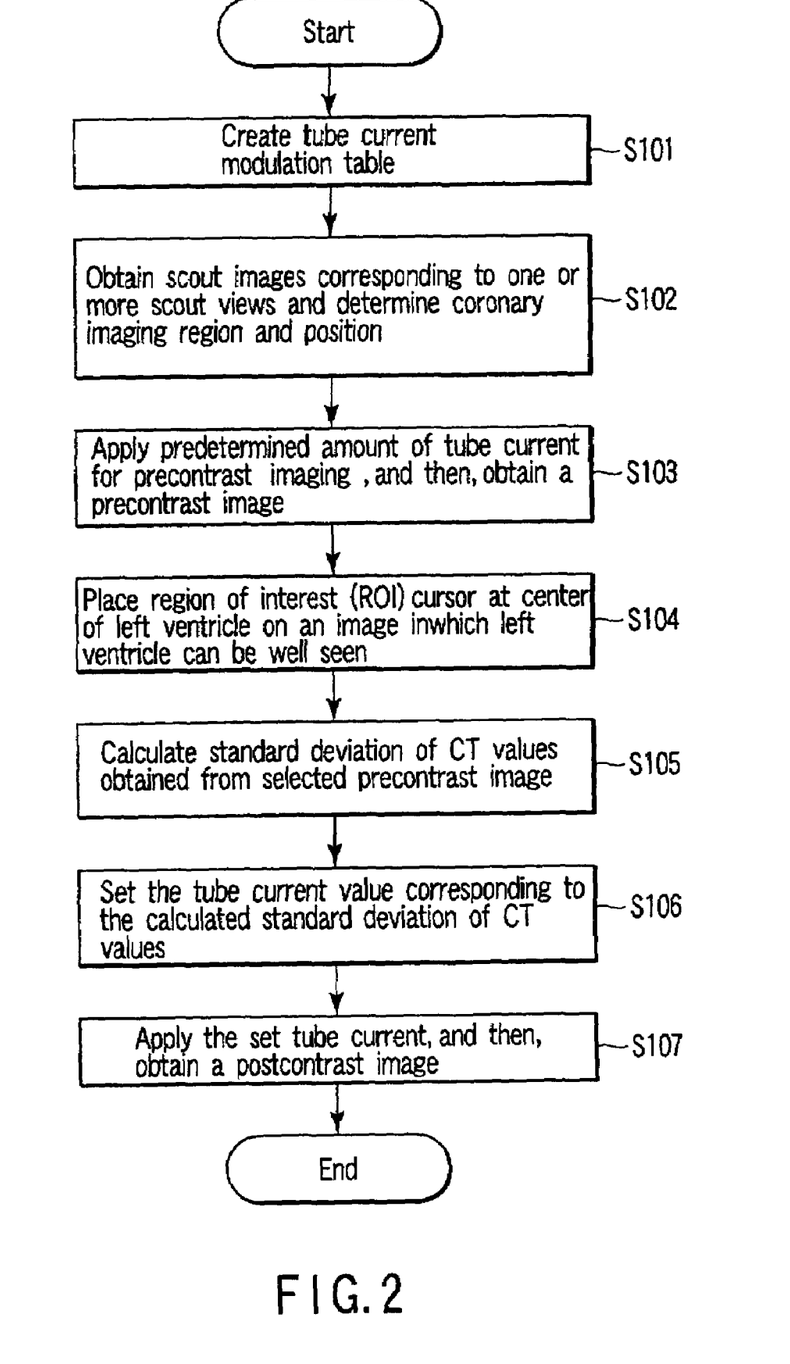
FIG. 2 is a flow chart of a coronary CT imaging process by the use of the CT system of FIG. 1.

FIG. 2 is a flow chart of a coronary imaging process by means of the CT system of FIG. 1. As illustrated in FIG. 2, a method for modulating an exposure dose utilizing a standard deviation of CT numbers in coronary CT angiography according to the present invention is roughly divided into scan control processes of first to fourth steps. The method is mounted on the central processing unit (3) of FIG. 1, or can be provided as a module controllable by the central processing unit.

The first step include the step (S101) of creating and storing a table for classifying and associating respective tube current modulation values and the standard deviation values with each other based on CT numbers automatically calculated in the X-ray CT system, i.e., the table as illustrated in Table 1.

The second step includes: the step (S102) of obtaining a scout image of a patient (a subject) relevant to one or more scout views, and then, determining data such as a coronary imaging region and a position; and the step (S103) of applying a predetermined amount of tube current (300 [mA]) before administration of a contrast medium, and then, obtaining at least one coronary image by means of pre-contrast imaging. The scanning is a non-contrast scanning executed before the post-contrast scanning. For instance, the scanning for the calcium scoring is applied. The scanning of this calcium scoring is non-helical scanning wherein the X-ray tube (21) moves on a circular orbit with respect to the subject. The post-contrast scanning is a helical scanning wherein the X-ray tube (21) moves on a helical orbit with respect to the patient.

The third step includes: the step (S104) of selecting at least one image from among the coronary images acquired before administration of the contrast medium, and then, placing a region of interest (ROI) cursor at the center of the left atrium in the selected image while setting the cursor in predetermined size (for example, 200 [mm$^2$]); and the step (S105) of calculating CT numbers and a standard deviation thereof relevant to the pre-contrast image. At this time, in the third step, a plurality of images can be selected from among a number of coronary images obtained before the administration of the contrast medium. In this case, a process can be constituted such that after the standard deviations of CT numbers relevant to the selected image are calculated an average value of the thus calculated standard deviations is obtained again to acquire a standard deviation of CT numbers to be associated with the tube current values, thereby making it possible to obtain a coronary image that enables more precise diagnosis on patients.

The fourth step includes: the step (S106) of setting, from the tube current modulation table, the tube current value that corresponds to the calculated standard deviation of the CT numbers; and the step (S107) of generating control signal for a scanning to control a tomography scan operation for obtaining a post-contrast image by the use of the set tube current value. The post-contrast study involve imaging anatomic locations that have homogenous fluid of sufficient amount at the center and a short scan range in which attenuation relevant to the Z-axis hardly varies.

Figure 3:
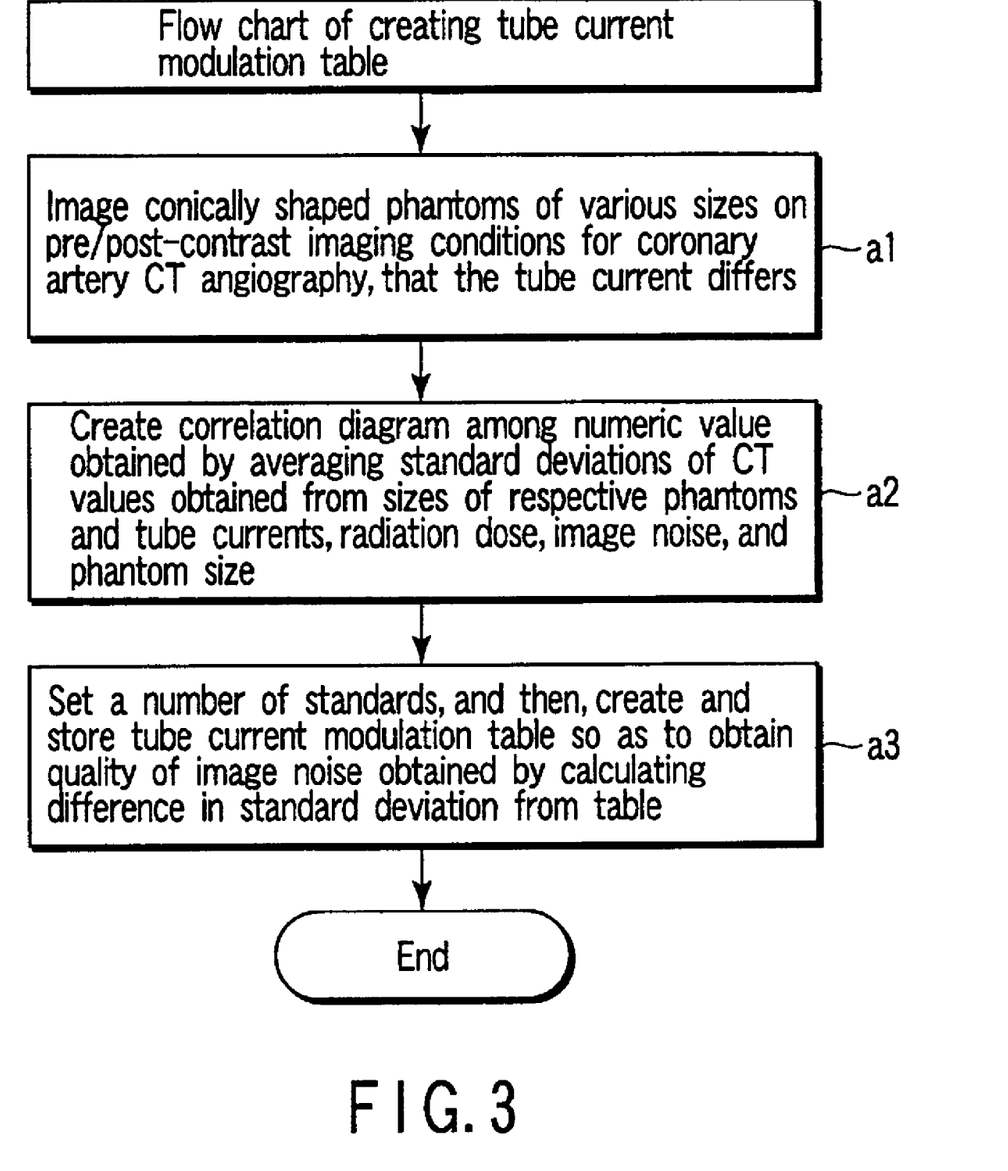
FIG. 3 is a flow chart of a process for generating a tube current modulation table in coronary CT angiography according to the present invention.

FIG. 3 is a flow chart illustrating a preprocessing course for creating a tube current modulation table in coronary CT angiography according to the present invention. The figure illustrates a detailed flow of processing relevant to the preprocessing course for creating the tube current modulation table at the first step to be carried out in the scan control process of FIG. 1.

As illustrated in FIG. 3, the above table can be created in advance through a course of sequentially executing a process that includes: the step (a1) of using a conically shaped phantom, or alternatively, setting a number of phantoms having different sizes from each other, sequentially applying tube currents of various magnitudes classified at predetermined intervals to the respective phantoms, and setting data such as a number of parameters, an exposure dose, image noise, and phantom size in the same manner as those for carrying out tomography imaging under the same imaging condition as that used for pre-contrast and post-contrast coronary CT angiography; the step (a2) of calculating standard deviations of CT numbers relevant to CT images under the same imaging condition that can be obtained from the phantoms, and then, comparably depicting a correlation therebetween; and the step (a3) of obtaining, from the table, one or more types of tube current values for obtaining an image noise level that serves as a level to be obtained based on a standard deviation of CT numbers calculated from a condition for applying a predetermined amount of tube current, and then, creating a table having tube current values that correspond to standard deviations of CT numbers.

Figure 4A:
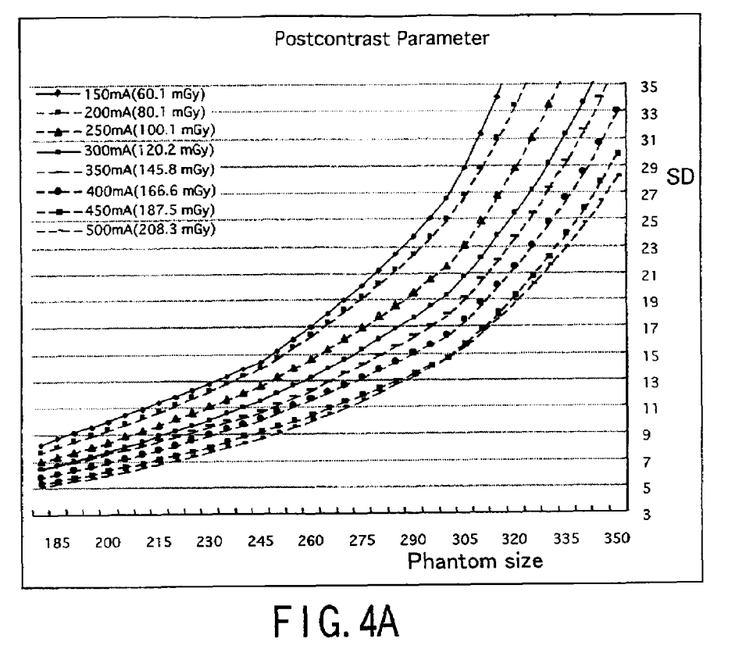
FIG. 4A is a graph produced by calculating and plotting standard deviation values of CT numbers from an image obtained by carrying out phantom imaging by the use of an imaging condition identical to that for coronary CT angiography before administration of a contrast medium.

FIG. 4A is a graph produced by calculating and plotting standard deviation values of CT numbers from an image obtained by carrying out phantom imaging by the use of an imaging condition that is identical to that for pre-contrast coronary CT angiography. A relationship between the noise level in the standard deviation values of CT numbers and the size of phantom scanned with pre-contrast parameter (120 kV X-ray tube voltages, 180 mm FOV, 4×3 mm collimation, sequential scan, prospective ECG gaiting, half reconstruction) are represented in FIG. 4A. Each exponential curve represents relationship between the phantom size and the standard deviation value at a given tube current.

Figure 4B:
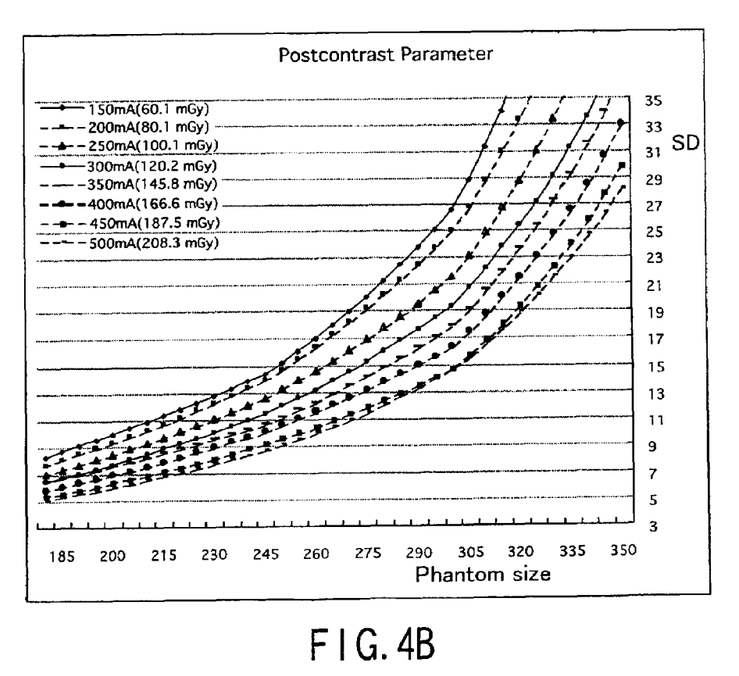
FIG. 4B is a graph produced by calculating and plotting standard deviation values of CT numbers from an image obtained by carrying out phantom imaging by the use of an imaging condition identical to that for coronary CT angiography after administration of a contrast medium.

FIG. 4B is a graph produced by calculating and plotting standard deviation values of CT numbers that can be obtained from an image obtained by carrying out phantom imaging by the use of an imaging condition that is identical to that for post-contrast coronary CT angiography. A relationship between the noise level in standard deviation values of CT numbers and the size of phantom scanned with post contrast parameter (120 kV X-ray tube voltages, helical scan, retrospective ECG gaiting, 64×0.5 mm collimation, pitch of 0.204, half reconstruction) are represented in FIG. 4B. Each exponential curve represents relationship between the phantom size and the standard deviation value at a given tube current. Radiation dose ($CTDI_{vol}$ expressed in mGy) in parenthesis increase linearly with tube current. The dose is scanner specific (other scanner may produce different radiation dose with same parameters) and the standard deviation value is 0.5-1.5 higher on pre-contrast image compare to post-contrast image as phantom size increase from 180 cm to 300 cm. The difference reflects difference of radiation dose from methods of ECG gaiting and reconstruction.

FIGS. 4A and 4B are graphs produced by numerically calculating and plotting standard deviation values (SD) of CT numbers that can be obtained from a CT system having a 64-row detector, in the case of carrying out tomography by sequentially applying tube currents at intervals of 50 [mA] in the range of 150 [mA] to 500 [mA] to a water-filled disk shaped phantom of which diameter (d) is in the range of 185 [cm] to 350 [cm]. The graphs are prepared by calculating and plotting standard deviation values of CT numbers with the use of formula 1 below. When a conically shaped phantom is used, the use of formula 1 becomes not necessary. In both of the two graphs, the results are obtained while an electrocardiographic signal is connected to a person positioned outside of a scan room (heart rate: 62 times), and all of the conditions including scan and reconstruction parameters are provided in the same manner as those in a practical condition. However, X-ray tube currents are differentiated while being increased from 150 [mA] to 500 [mA] at intervals of 50 [mA]. The standard deviations of CT numbers are illustrated by the graphs produced by measuring a cursor in size of 200 [$mm^2$] to the center from 64 sets of images (a total of 256 images) that consist of images that conform to the four conditions, and then, obtaining an average number.

Figure 4C:
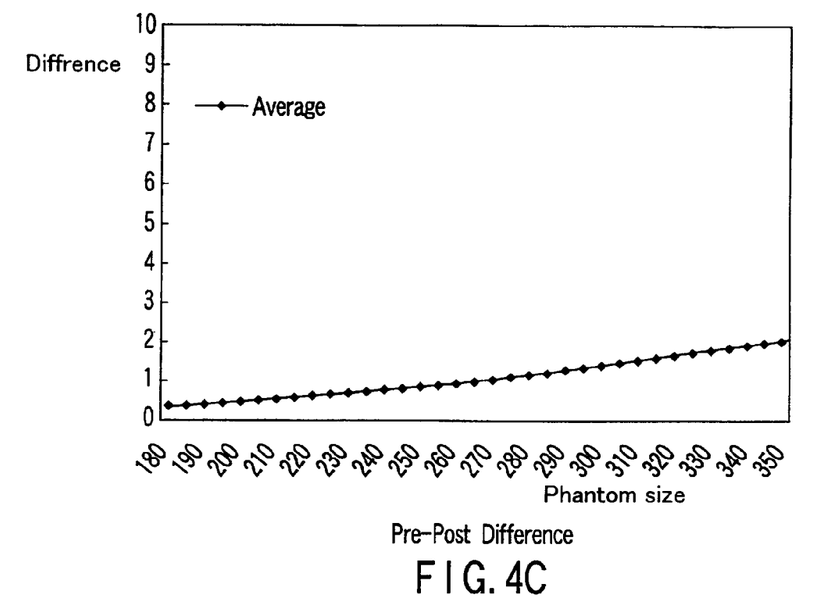
FIG. 4C is a graph produced by calculating and plotting differential values of standard deviations of CT numbers of a phantom image using two imaging conditions.

FIG. 4C is a graph produced by calculating and plotting differential values of standard deviation values of CT numbers of a phantom image that uses two imaging conditions. This graph depicts a horizontal line of which a gradient is almost uniform below 300 [cm] at which desirable image quality can be obtained, although a slight curve is shown.

$$CTDI_w \times \sigma^2 \propto E^{(\mu \cdot D)} \qquad \text{[Formula I]}$$

In the formula, $\sigma^2$ is an image noise, i.e., a standard deviation of CT numbers; $CTDI_w$ corresponds to an exposure dose relevant to a water phantom, i.e., a tube current; E is a natural logarithm value, which is constant; $\mu$ is an intermediate value of a radiation attenuation coefficient of water (phantom) in a constant tube voltage; and D is a diameter of an imaging site of the phantom. The above formula 1 shows a correlation that, if a diameter of an object (phantom) increase or a tube current decrease, an image noise increases while depicting an exponential curve. As is evident from the formula 1 above, CT image quality, a tube current and patient size have a correlation that, if the diameter (D) of an imaging object increases or a tube current ($CTDI_w$) decreases, an image noise ($\sigma$), i.e., a standard deviation of CT numbers increases while depicting an exponential curve.

Figure 4D:
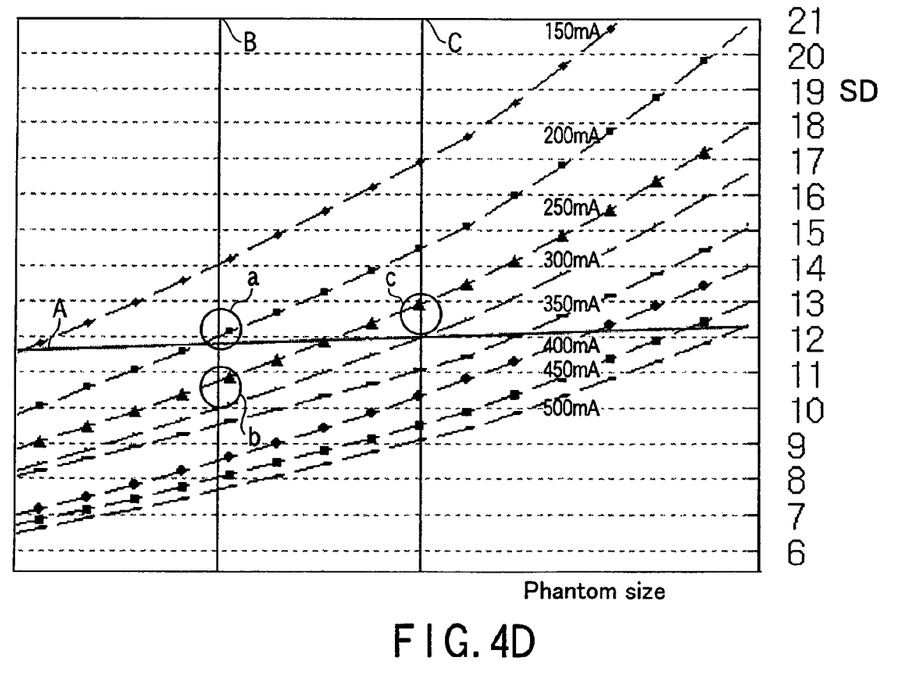
FIG. 4D illustrates calculating process of the tube current modulation table (Table 1).

FIG. 4D illustrates calculating process of the tube current modulation table (Table 1); for a desired target level of 12 in a patient who has SD of 10 on precontrast images obtained at predetermined tube current (300 mA in this example), 1) line A is placed at a level where the 300 mA exponential curve is crossing SD value of 12 (circle a). The horizontal line with positive angle to the right (slope A) is imported from FIG. 4C, and it shows increasing difference of SD values between pre and post contrast images as phantom size increases from 180 cm to 300 cm and it reflects difference of radiation dose between two parameters, 2) a vertical line B is placed at a point where the 300 mA exponential curve is crossing SD value of 10 (circle b) (obtained from precontrast images of the patient), 3) read a crossing point of vertical and transverse lines, it is between exponential lines of 200 mA and 250 mA closer to 200 (circle c) mA and, 4) for a patient with measured SD value of 12, crossing point is located at exponential curve of 300 mA. (line C). In other words, X-rays are irradiated by the tube current 210 mA in a helical scanning to obtain the post-contrast images when the SD value of the pre-contrast images obtained by non-helical scanning is nine and projection data is collected. The post-contrast image of SD value 12 can be obtained by reconstructing and processing this projection data.

In particular, the horizontal line with a positive slope from left to right in FIG. 4D serves as a line expressing, by a value corresponding to a pre-contrast image, post-contrast image quality (standard deviations of CT numbers). In this example, the line is a line that permits the standard deviation value of the post-contrast image to become 12.

An operation and function or advantageous effect of the present invention constructed above will be described as follows.

From a state that a table, produced by classifying and associating respective tube current modulation values by means of CT numbers and their standard deviation values, automatically computed and presented by means of X-ray imaging in a CT system, is stored in the storage section (8) of FIG. 1 (S101), the second step is carried out by sequentially executing the step (S102) of obtaining a scout image of a patient with respect to one or more scout views such as frontal or side views, and then, determining data such as an imaging region and a position; and the step (S103) of applying a predetermined amount of tube current positioned at the center on the chart of FIG. 4A (300 mA in this chart) before administration of a contrast medium, and then, carrying out pre-contrast imaging, thereby obtaining at least one coronary image.

Next, at the third step, at least one image is selected from the pre-contrast coronary images (images with streaking artifacts are avoided). Then, a region of interest (ROI) cursor is set in a predetermined size, for example, 200 [mm$^2$], and placed (S104) at the center of the left atrium in the selected image, and then, CT numbers and a standard deviation thereof relevant to the pre-contrast images are calculated (S105).

More desirably, four images, for example, are selected from among a number of coronary images obtained before administration of a contrast medium; standard deviations of CT numbers relevant to the selected images are calculated, by means of the method described previously, and then, an average value relevant to the calculated standard deviations is obtained again; and a standard deviation of CT numbers associated with the tube current values described previously is obtained. In this manner, the standard deviations of the CT numbers can be obtained at more precise values with respect to patients, and then, a coronary image enabling more precise diagnosis can be obtained.

Lastly, at the fourth step, the tube current values corresponding to the standard deviations of CT numbers calculated at the third step are set (S106) from the tube current modulation table; and then, an operation of the X-ray tube (21) is controlled by means of the thus set tube current values, making it possible to control (S107) a tomography scan operation for obtaining a post-contrast image. Therefore, the present invention can utilize a standard deviation of CT numbers as a precise and practical intervening variable for individual modulation of tube currents, thus making it possible to obtain uniform image quality required for precise diagnosis of coronary arteries, and, at the same time, to reduce an exposure dose while properly maintaining image quality in a small patient.

TESTING EXAMPLE

An experimental CT image cannot be directly obtained from a patient. Thus, phantom studies are conducted to carry out CT imaging under the same conditions as practical coronary imaging conditions, with the use of circular disk shaped phantoms (180, 245, 300, 350 cm) of which diameters are different from each other, the phantoms having been produced by filling them with water, which has an attenuation analogous to a patient's body. In CT coronary imaging, pre-contrast imaging and post-contrast imaging are carried out. In both pre-contrast and post-contrast imaging, the imaging information is recorded at the same time as that for ECG signal generation. In the case of coronary CT angiography, in pre-contrast imaging, a prospective ECG gating technique (a method for emitting radioactive rays by utilizing an electrocardiogram while selecting only a period at which the heart does not take a motion relatively) is used. In the post-contrast imaging, retrospective ECG gating technique (a method for constructing an image while selecting only a site with the least motion, based on information obtained by emitting radioactive rays to all cycles of the heart, and then, carrying out imaging) is used.

In the phantom study of the present invention, the results were obtained using both of the two techniques while an electrocardiographic signal is connected to a person positioned outside of a scan room, and all of the conditions are provided in the same manner as those under a practical condition with the exception that X-ray tube currents are differentiated while being increased from 150 [mA] to 500 [mA] at intervals of 50 [mA].

The obtained results graphically depict pre-contrast (FIG. 4A) and post-contrast (FIG. 4B) correlations between a size of phantom (patient's size) and an image signal noise level (standard deviation of CT numbers), and the values of the phantom size were obtained by the use of formula 1 described previously. This chart shows how the X-ray exposure dose changes depending on the patient's size in order to obtain a predetermined image quality (signal noise level). In addition, a chart was produced by obtaining the difference between the pre-contrast and post-contrast standard deviations of CT numbers.

Then, coronary image quality evaluation can be made in a post-contrast image. (A pre-contrast image is used to precisely determine an examination position after measuring a degree of calcification, as described previously. If calcification is large in amount, the frequency or degree of coronary artery atherosclerosis increases proportionally.) It is an objective of this evaluation to obtain a uniform, predetermined noise level in a post-contrast image, (the lower the noise level is, the better an image becomes. However, an utmost effort must be made so as to use a minimal required amount of X-rays because the X-ray exposure dose, specified as a carcinogen, becomes high, especially in the overlying radiosensitive breasts.). Among the pre-contrast phantom images, a standard deviation of images using 300 [mA] was obtained; a tube current value for obtaining a standard deviation level was obtained from the table; and a table of tube current values together with the standard deviation values was produced. A difference between pre-contrast and post-contrast standard deviations (SD) values occurs because ECG gating methods are different from each other (prospective and retrospective) and the scan methods are also different from each other (a pre-contrast scanning is used a non-helical scanning, a post-contrast scanning is used a helical scanning).

A difference in SD values due to a difference between the two scan methods is about 0.5 on average in a small phantom (185 cm) and is in the order of 2.0 in a 300 cm phantom. In the chart of FIG. 4D described previously, a difference of about 0.5 to 1.5 was shown in the range such that improvement is possible at the maximum tube current of the equipment used in this testing example.

According to the present invention described above, standard deviation of image signal intensity (CT numbers) is directly measured from a pre-contrast image, and then, a tube current is predetermined in accordance with a tube current modulation table and post-contrast scanning is executed under the predetermined tube current. Therefore, there can be provided a CT system that is capable of obtaining uniform image quality required for precise diagnosis, and, in particular, that is capable of making a further precise selection of a tube current by means of a direct measurement value obtained from an image of a patient's scan site, an image of uniform quality to be obtained by providing all the processes as a module, and then, mounting the module in a CT imaging system.

In addition, according to the present invention, it is possible to obtain uniform image quality due to individual modulation of a tube current while directly obtaining a precise signal noise level from a pre-contrast image. Therefore, the method of the invention is more precise than that which uses body weight, height, dimensions or attenuation value obtained from topogram(s) that do not reflect scan methods or parameters. As a result, it becomes possible to drastically reduce a radiation exposure dose while properly maintaining image quality in a small patient.

In this particular instance, the present invention attains its advantageous effect in coronary angiography, but it can very easily be applied to the study of organs that contain homogenous fluid at the center and have short scan ranges in which the attenuation relevant to the Z-axis hardly varies, such as those adjacent to the bladder containing the homogenous fluid of urine which is analogous to blood in the example of the chambers of heart, i.e., study of reproductive organs such as prostate as well as bladder itself. It should be noted that coronary CT angiography is a particularly challenging type of CT angiography due to the rapid movement of the heart and the ECG gating technique that is necessary to overcome such movement. Because the new invention works to tackle the affects of all the varying parameters on the image quality, the removal of the ECG gating parameter, such as to imitate instances of other types of CT angiography, would have been the equivalent of removing an obstacle and would not have negatively affected the diagnostic quality of the final images and therefore, the results of the study.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radiation dose modulation apparatus controlling a radiation dose in a coronary CT angiography that utilizes an X-ray CT system including a multi-row detector, the apparatus comprising:
    a tube current modulation table storage unit which classifies standard deviation values of CT numbers calculated from at least one pre-contrast CT image into a series of levels, stores at least one tube current modulation table in which the levels are associated with corresponding tube current modulation values, for each of a plurality of desired noise level standard deviations; and
    a processing unit configured to calculate a standard deviation of the CT numbers from the at least one pre-contrast CT image, to determine the tube current value corresponding to the calculated standard deviation for a desired noise level standard deviation, from the at least one tube current modulation table, and to control a scan operation for obtaining a post-contrast CT angiography in accordance with the determined tube current value.

2. The radiation dose modulation apparatus according to claim 1, wherein tube current modulation values for obtaining specific image qualities correspond to the levels in the at least one tube current modulation table.

3. The radiation dose modulation apparatus according to claim 1, wherein said processing unit is configured to calculate standard deviations of CT numbers relevant to a plurality of images selected from among pre-contrast images, to calculate an average value of the calculated standard deviations, and to identify the tube current value corresponding to the calculated average value from the tube current modulation table.

4. A method for obtaining one or more scout images of a patient relevant to one or more scout views, determining an imaging region based on the scout images, obtaining at least one pre-contrast image on a predetermined tube current value, determining an imaging range and position of a patient based on the pre-contrast images and modulating radiation dose in post-contrast CT angiography that utilizes an X-ray CT system including a multi-row detector, the method comprising the steps of:
    (a) creating and storing at least one table having tube current modulation values classified by means of a standard deviation of CT numbers through examinations of phantoms of varying sizes using different sets of fixed parameters that will be used in practice for both pre and post-contrast studies, with the exception of variable tube current;
    (b) selecting an image from among at least one pre-contrast image obtained through application of a predetermined amount of tube current before administration of the contrast medium, resizing the selected image to a predetermined size and placing a region of interest (ROI) cursor at one of a left atrium, another cardiac chamber, and an aorta in the selected image, and calculating a standard deviation of CT numbers obtained from the pre-contrast image; and
    (c) setting a post-contrast tube current value by accessing a tube current modulation table created through phantom examination, using the calculated standard deviation of the CT numbers and a desired noise level standard deviation, and controlling a CT imaging and scanning operation for obtaining a post-contrast image by using the set post-contrast tube current value.

5. The radiation dose modulation method according to claim 4, wherein the tube current modulation table is configured such that a number of tube current modulation values for obtaining one or more types of image qualities are associated with the respective levels.

6. The radiation dose modulation method according to claim 4, wherein if a plurality of images are selected from among a number of images obtained before administration of the contrast medium, each of standard deviations of CT numbers relevant to the selected images is calculated to obtain an average value of the calculated standard deviations, the method further comprising obtaining a standard deviation of CT values to be associated with the tube current values.

7. The radiation dose modulation method according to claim 4, wherein, in the creating step, if a CT angiography of a prostate is to be performed, each of the standard deviation of CT numbers is obtained from precontrast images of a bladder.

8. An X-ray CT apparatus, comprising:
    an X-ray tube;
    an X-ray detector configured to detect X-rays transmitted through a subject;
    a noise index calculating unit configured to calculate a noise index from a pre-contrast CT image for the subject;
    a tube current value determining unit configured to determine a tube current value in a scanning for obtaining a post-contrast image of the subject based on the calculated noise index and a desired noise level standard deviation; and
    a control unit configured to control a tube current of said X-ray tube in a scanning after a contrast medium administration in accordance with the determined tube current value.

9. The X-ray CT apparatus according to claim 8, wherein said noise index calculating unit calculates the noise index in a partial region of pre-contrast image.

10. The X-ray CT apparatus according to claim 9, wherein the partial region is set to a region including at least one of a left atrium, a cardiac chamber, and an aorta of the subject.

11. The X-ray CT apparatus according to claim 8, wherein said noise index calculating unit calculates an average number of calculated noise indexes of a plurality of CT images.

12. The X-ray CT apparatus according to claim 8, wherein said tube current value determining unit stores at least one table in which tube current values correspond to classes related to the desired noise level standard deviation and a measured noise index, and said tube current value is determined by using the at least one table.

* * * * *